United States Patent [19]

Scodari et al.

[11] Patent Number: 5,560,906
[45] Date of Patent: Oct. 1, 1996

[54] NON-ALCOHOLIC ANTIMICROBIAL MOUTHWASH FOR REMOVAL OF DENTAL PLAQUE

[75] Inventors: Nicholas F. Scodari, Phillipsburg; Ronald L. Chattman, Somerville, both of N.J.

[73] Assignee: Oral Technology Laboratories, Inc., Coraopolis, Pa.

[21] Appl. No.: 410,976

[22] Filed: Mar. 27, 1995

[51] Int. Cl.$^6$ ................................ A61K 7/16; A61K 7/22
[52] U.S. Cl. ................................................ 424/54; 424/49
[58] Field of Search ............................................ 424/49–50

[56] References Cited

U.S. PATENT DOCUMENTS

| | | | |
|---|---|---|---|
| 3,296,079 | 1/1967 | Griffin | 167/93 |
| 4,122,205 | 10/1978 | Burge et al. | 426/548 |
| 4,146,499 | 3/1979 | Rosano | 252/186 |
| 4,200,659 | 4/1980 | Willis et al. | 426/534 |
| 4,251,548 | 2/1981 | Ogawa et al. | 426/3 |
| 4,277,511 | 7/1981 | Blizniak et al. | 426/548 |
| 4,568,480 | 2/1986 | Thir et al. | 252/312 |
| 4,657,758 | 4/1987 | Goldenberg et al. | 424/49 |
| 4,666,708 | 5/1987 | Goldemberg et al. | 424/49 |
| 4,835,002 | 5/1989 | Wolf et al. | 426/590 |
| 4,842,766 | 6/1989 | Blohm et al. | 252/309 |
| 4,911,918 | 3/1990 | Kiyoshige et al. | 424/50 |
| 5,149,521 | 9/1992 | Hirose et al. | 424/58 |
| 5,283,056 | 2/1994 | Chung et al. | 424/49 |
| 5,284,648 | 2/1994 | White et al. | 424/49 |
| 5,292,527 | 3/1994 | Konoda | 424/54 |
| 5,407,664 | 4/1995 | Konopa | 424/54 |

*Primary Examiner*—Shep K. Rose
*Attorney, Agent, or Firm*—Robert M. Skolnik

[57] ABSTRACT

A pleasant tasting antimicrobial mouthwash formulation which maintains clarity for removal of dental plaque where no alcohol, sugar, artificial sweeteners are used making it suitable for safe use by alcoholics, diabetics, persons under medical treatment or taking medications which prelude the use of alcohol, hospitalized patients, prison inmates, minors and all other persons who can not or should not subject themselves to alcohol, sugar, or artificial sweeteners. The formulation consists of water, glycerin, sodium benzoate, cetylpyridinium chloride, citric acid, maltol, xylitol, a flavoring agent to give a pleasant though biting taste, and a coloring agent.

15 Claims, No Drawings

NON-ALCOHOLIC ANTIMICROBIAL MOUTHWASH FOR REMOVAL OF DENTAL PLAQUE

FIELD OF THE INVENTION

This invention relates to a pleasant tasting antimicrobial, antiplaque mouthwash formulation, which maintains stability and clarity, free of alcohol, sugar and artificial sweeteners, that kills bacteria through antimicrobial action, thereby loosening plaque on teeth so that the plaque can be more easily removed during brushing or with additional dental rinsing, or by any other conventional method of cleaning the teeth.

DESCRIPTION OF THE PRIOR ART

U.S. Pat. No. 3,591,675, issued Jul. 6, 1971, discloses a brushless dentifrice consisting of carbon dioxide, ethyl alcohol, cetylpyridinium chloride and benzethonium chloride.

U.S. Pat. Nos. 4,666,708, issued May 19, 1987 and 4,657,758, issued Apr. 14, 1987, disclose a dental rinse for loosening plaque. This patent teaches a rinse including sodium benzoate and demonstrates that such a rinse is effective in loosening plaque. The composition employed in the patent includes: water, 65% to 95%; alcohol, 5% to 35%; sodium lauryl sulfate, 1% to 10%; and sodium benzoate, 2%.

While commercially successful, the formulation of the patent has proven to be ineffective in and/or not useable by certain individuals because of its content of alcohol, saccharine and dye.

U.S. Pat. No. 4,132,770, issued Jan. 2, 1979, discloses an aqueous oral product including sodium bicarbonate in solution, a flavor oil where desired, and at least one emulsifying agent for said flavor oil, and a dye if color is required; there may optionally be included a cosmetic alcohol, a humectant and sweetening agents.

U.S. Pat. Nos. 3,864,472, issued Feb. 4, 1975 and 3,947,570, issued Mar. 30, 1976, disclose lemon oil containing flavored mouthwash free from unpleasant tasting lemon oil degradation components comprising water, lemon oil, non-ionic surfactant, humectant and buffering agent.

U.S. Pat. No. 4,132,770, issued Jan. 2, 1979 discloses a mouthwash with a pH of 8.0–9.3 including sodium bicarbonate and an emulsifying agent.

U.S. Pat. No. 4,150,151, issued Apr. 17, 1979 discloses essentiality a mouthwash with sodium dodecyl sulfate and sodium tetradecyl sulfate in various ratios.

U.S. Pat. No. 4,205,061, issued May 27, 1988, discloses a combination of antimicrobial ingredients including a halogenated salicylanilide and a quaternary ammonium compound.

U.S. Pat. No. 4,323,551, issued Apr. 6, 1982, discloses a mouthwash composition including cetylpyridinium chloride and tetrapotassium pyrophosphate.

U.S. Pat. No. 4,370,314, issued Jan. 25, 1983, discloses an antibacterial oral composition containing a cationic quaternary ammonium antibacterial antiplaque agent and an additive which reduces staining including alkali metal bicarbonate and benzethonium chloride or cetylpyridinium chloride.

U.S. Pat. No. 4,606,912, issued Aug. 19, 1986, discloses a mouthwash and a method for making same which includes calcium chloride, sodium fluoride, disodiummonohydrogen phosphate, glyceric acid and sodium chloride.

U.S. Pat. No. 4,861,582, issued Aug. 29, 1989, discloses dental compositions containing bicarbonate anion in combination with a monovalent anion such as fluoride, chloride or thiocyanate and methods of them in anticarogenic, antiplaque and antiperiodontopathaic therapy.

Other formulations of non-alcoholic mouthwashes are prone to cloud on aging because of the lack of alcohol for solubilization. In such prior art formulas, solubilizers were added in the flavoring; however, these solubilizers are esters which are not particularly stable. As the esters break down, the product clouds and, over time, shows precipitation.

Still other formulations using sodium bicarbonate and citric acid produced effervescence which resulted in undesirable by-products.

Poor taste in terms of lack of bite and a back note of a soapy nature has also been characteristic of many prior art non-alcoholic mouthwash preparations.

SUMMARY OF THE INVENTION

The present invention meets the need in the art of dental preventive medicine for a pleasant tasting oral hygiene formulation which maintains its clarity that can be safely used by those individuals who cannot or should not use a mouthwash containing alcohol, sugar, or artificial sweeteners.

In the formulation of the invention, no alcohol, sugar, artificial sweeteners are used. The formulation consists of water, glycerine, sodium benzoate, cetylpyridinium chloride, citric acid, maltol, xylitol and a mint/cinnamon flavor.

Water is the carrier. It must meet USP criteria for manufacture and have a pH of between 5.5 and 7.0. Glycerine serves as a humectant to provide body and a textual feel to the water. Glycerine also acts as the sweetener. Sodium benzoate is the anti-plaque and anti-calculus material. Cetylpyridinium chloride is a quaternary ammonium compound which is active against bacteria commonly found in the mouth. Flavor is added to produce a pleasant bite in the quantity of 85% mint and 15% cinnamon. Citric acid is also added to stabilize the pH of the formulation. The pH of the present invention is between 6.6±0.4. Maltol is a flavoring agent to impart a fresh flavor. Xylitol is used as a nutrient.

The present invention can be used by persons such as prison inmates, alcoholics or member of the police force or other persons who cannot subject themselves to alcohol for physiological, psychological, social or job related reasons. Of additional importance is the ability to use the present invention on chemotherapy patients.

A principal object of the present invention is to provide a mouthwash which assists in removing dental plaque. Another object of the invention is to provide an antimicrobial antiplaque mouthwash that destroys the microorganisms that play a key role in the etiology of plaque. A still further object and advantage of this invention is the provision of a mouthwash which aids in the reduction of caries formation and which inhibits the development of calculus and oral diseases associated with excessive plaque formation such as gingivitis and periodontitis.

A further object is the provision of a mouthwash which contains substances which enable its use by persons whose ingestion of alcohol must be controlled and/or eliminated while maintaining taste and clarity. Another object of the invention is to provide an effective plaque removing dental mouthwash which can be used by chemotherapy patients. A still further object of our invention is the provision of a mouthwash formulation which contains no artificial sweeteners. Another object of the invention is the provision of a non-alcoholic mouthwash which does not have problems in taste. A further object and advantage of our invention is the provision of a mouthwash which is stable with clarity.

These as well as further objects and advantages of the invention will become apparent to those skilled in the art from a review of the following detailed specification of our invention.

DETAILED DESCRIPTION OF THE INVENTION

In the formulation of the invention, no alcohol, sugar, or artificial sweeteners are used. The formulation consists of water, glycerin, sodium benzoate, cetylpyridinium chloride, citric acid, maltol, xylitol, a coloring agent and mint and cinnamon flavoring.

Plaque consists of about 80% live bacteria in a polysaccharide matrix. Therefore, it is desirable for a mouthwash to possess significant antibacterial properties in order to eliminate or retard the growth of the bacterial colonies present in plaque. The antimicrobials, sodium benzoate and cetylpyridinium chloride employed in our invention function to significantly reduce the number of bacteria in the oral cavity, thereby retarding development of plaque, caries and halitosis.

Sodium benzoate is an antimicrobial agent with antiseptic properties that reduces the number of plaque producing, odor causing bacteria in the oral cavity. Sodium benzoate also acts as a preservative and as an antiplaque agent.

Cetylpyridinium chloride is a quaternary ammonium compound which is an antimicrobial agent active against most common bacteria found in the mouth. Cetylpyridinium chloride also possesses antiseptic properties and acts as a detersive agent.

Citric acid is a buffering agent. By adjusting the hydrogen ion concentration, citric acid stabilizes the pH of the formulation. It also has been determined to have antimicrobial properties.

Glycerine serves as a humectant to provide body and a textual feeling to the liquid carrier. Glycerin also acts as a sweetener. Glycerine is included in 53 Fed. Reg. 2436 as safe and effective in oral health care drug products.

Maltol serves as a flavoring agent to impart a fragrant, caramel-like odor. We believe that maltol masks any soapy taste in our invention. Xylitol serves as a nutrient in various anticaries preparations such as chewing gums as reported in 1993 in the *Journal of Dental Research*, Vol. 72 (Special Edition), Abstract 1945, by Makinen, et al., and in HEALTH, July/August, 1993, page 14.

The mouthwash comprises a solution with water as the liquid carrier. The water meets USP criteria for manufacture, having a pH of between 5.5 and 7.0. The pH of the invention is 6.6±0.4, which is slightly acidic since sodium benzoate functions more effectively in an acidic solution.

Unlike other commercial mouthwashes, the present invention is free of alcohol. Alcohol is absorbed sublingually. It also has been documented that, although mouthwashes should be expectorated, alcoholics, including those who are members of the prison population, are likely to be abusers of any substance containing alcohol, including mouthwashes. Therefore, the present invention is suitable for safe use by alcoholics and others who cannot, or should not use alcohol because of physiological, psychological, social or job related reasons.

Of additional importance is the ability to use the present invention on chemotherapy patients. It is known that patients undergoing chemotherapy should not ingest even minute amounts of alcohols. Chemotherapy causes the parotid glands to produce an insufficient amount of saliva. In turn, an insufficient amount of saliva in the mouth contributes to the breakdown of tooth enamel (dental caries). Therefore, the present invention is suitable for safe use by those undergoing chemotherapy.

The present invention is free of sugar. Sugar is converted in the mouth to acid, a major factor in the etiology of dental caries and in the formation of plaque. The metabolization of sugar by bacteria produced toxins and waste products that exude into the gums, inflaming them, thereby initiating gum disease. It is also known that sugar should not be ingested by diabetics and that sugar has other deleterious effects. Therefore, the present invention is suitable for safe use by diabetics and other who cannot, or should not, use sugar.

The present invention is free of sodium saccharin. Sodium saccharin, like alcohol, is absorbed sublingually. Sodium saccharin has been found to be carcinogenic in laboratory animals, specifically-rats and mice. Therefore, the present invention is suitable for safe use by those who cannot, or should not use saccharin.

The mouthwash is applied to the surface of the teeth, gums and oral cavity by using two tablespoons of the oral rinse, circulating it throughout the mouth for a minimum of ten seconds in order to thoroughly soak the teeth and gums, then discharging the oral rinse from the mouth. The oral rinse should not be swallowed. Immediately thereafter, the teeth should be thoroughly brushed, using a conventional toothbrush and dentifrice. Regular and correct use of this invention is intended to significantly reduce the number of bacteria present in the oral cavity and to inhibit the formation of plaque. This, in turn, will help prevent or ameliorate plaque associated oral diseases, such as gingivitis and periodontitis, and reduce the incidence of dental caries.

The invention underwent analytical testing—by extraction and titration—to ensure that cetylpyridinium chloride and sodium benzoate in the non-alcoholic mouthwash is stable for a period of at least three months in sealed bottles at ambient temperatures of up to 40° C. at 70% relative humidity.

Microbiological testing of the invention was undertaken to ensure that the mouthwash is free from bacteria, mold and yeast. In compliance with the guidelines set forth in *US Pharmacopoeia* (Vol. 21), the mouthwash was inoculated with various organisms and a rapid reduction, both in their number and activity, was observed. In the sample tested, the TBS/gm (ml) (total bacteria count) was less than 10; there was no growth in the broth enrichmen' gram stain test; the TMC-TYC/gm (ml) (total mold -yeast count) was less that 10, and there was no growth in the TMC-TYC broth. For group I bacteria, group II bacteria, and group III fungi-yeast, the percentage of reduction was 99.9%, at the end of 24 hours and 99.9% at the end of one week. The invention passed USP XXII challenge testing.

The mouthwash formulation of the invention comprises a solution with a pH of 6.6±0.4. The liquid carrier is water (86.15), which meets USP criteria for manufacture and has a pH of between 5.5 and 7.0. The pH of the invention is 6.6±0.4, which is slightly acidic since sodium benzoate functions more effectively in an acidic solution.

Dissolved in the liquid carrier are the following components in the following weight percents; glycerine, FCC (19.00); sodium benzoate, FCC (0.30); cetylpyridinium chloride, USP (0.045); citric acid, FCC (0.10); maltol, FCC (0.10); xylitol (1.00); mint/cinnamon flavor (0.40, 85% mint, 15% cinnamon); and FDC red #40 (0.0012). These ingredients may vary by 15% ±.

This preparation was evaluated in a twenty-one day controlled use test. The preparation evaluated was prepared in accordance with the invention with a pH of 6.6 as follows: water, (86.15); glycerine, USP (12.50); sodium bicarbonate, USP (0.50); sodium benzoate (0.30); cetylpyridinium chloride (0.045); and citric acid, USP (0.10) and flavoring agents, spearmint and peppermint. The control was a flavored water rinse.

The oral rinse and the control were distributed to separate groups containing eight subjects each. The subject's ages ranged from 18 to 57 years. Baseline oral examinations were performed on all subjects in this study. Standard evaluations were done using mouth mirrors, explorers and potassium hydroxide disclosing tablets.

The scoring for gingivitis was based upon the papillary marginal-gingivitis index (PMGI Loe & Silness). The PMGI scores gingivitis on papillar and margins on the facial and lingual gingiva of natural teeth. In this method, the severity of gingivitis is expressed by the average of individual scores for each subject divided by the number of papillary and marginal units examined per subject. The study commenced with a PMGI score of at lease 2.0 prior to start. This particular scoring range exhibits moderate inflammation, moderate glazing, redness, edema and enlargement.

The plaque scoring system (Quigley & Hein) is a quantitative estimate of the amount of plaque present on the buccal, labial and lingual surfaces of the teeth. All subject examined had some level of plaque present. When this was not attainable, subjects were to refrain from brushing for two days prior to re-examination.

All subjects were instructed in the proper techniques for brushing teeth and the use of the mouthwash. Two brushings were to be performed daily followed by a double water rinse. Participants were instructed to rinse twice daily with the oral rinse or water control using measured 20 milliliter portions for 30-second periods. The rinse was to occur after brushing and a double water irrigation.

The results of this evaluation are set forth in the following where PI is the plaque index and PMGI is the gingivitis index.

|  | PI | PMGI |
|---|---|---|
| BASELINE RESULTS | | |
| Oral Rinse | 1.88 | 2.38 |
| Placebo | 2.75 | 2.13 |
| SEVEN DAY RESULTS | | |
| Oral Rinse | 1.88 | 2.38 |
| Placebo | 2.75 | 2.25 |
| TWENTY-ONE DAY RESULTS | | |
| Oral Rinse | 1.25 | 1.50 |
| Placebo | 2.88 | 2.25 |
| % REDUCTION | | |
| Oral Rinse | 33.5% | 36.9% |
| Placebo | — | — |

Among the factors that can significantly influence a solution's microbial activity is its pH. Extremes of a solutions' acidity or alkalinity effectively limit growth of microorganisms, pH 4.5 to 9 being a limiting range for many organisms. Furthermore, for many weak acids, antimicrobial activity is primarily attributable to the undissociated molecule; it is the undissociated acid molecules that are responsible for antimicrobial activity since they are able to pass through cell membranes more readily than the charged molecules.

The effect of pH on the activity of certain antimicrobial compounds is well known (Albert, 1951). It has been demonstrated that only the undissociated molecules of benzoic acid (sodium benzoate) are toxic to microorganisms; that the concentration of non-ionized molecules is dependent on the pH of the medium (Rahn and Conn, 1944); and that benzoic acid (sodium benzoate) is a more effective antimicrobial agent in acidic rather that neutral solutions. It has been further demonstrated that benzoic acid (sodium benzoate) is effective against bacteria in acid media at concentrations of 0.1% and in neutral media at concentrations of 0.2% (Gabel, 1921). The level of sodium benzoate in the invention is 0.30. The antimicrobial action is further potentiated by the addition of cetylpyridinium chloride.

The use of solvents other than water can influence antimicrobial activity by virtue either of the inherent toxicity of the solvent or through its effect on thermodynamic activity of antimicrobial agents. A nontoxic solvent such as glycerine appears to have little negative influence on microbial growth unless it is used in concentrations of 20% to 50% (Barr and Tice, 1957).

The level of glycerine in the mouthwash is carefully balanced in order to provide the preferred amount of body to the solution yet not interfere with the antimicrobial activity of the invention.

In order to advantageously enhance the antimicrobial properties of the mouthwash, sodium benzoate is included in the formulation. Sodium benzoate—the sodium salt of benzoic acid—is an antimicrobial agent with antiseptic properties that effectively reduces the number of bacteria in the oral cavity; sodium benzoate also functions as a preservative and an antiplaque agent.

Cetylpyridinium chloride, a quaternary ammonium compound, is an antimicrobial agent active against staphalococcus and streptococcus species as well as other bacteria. Cetylpyridinium chloride also possesses antiseptic properties and acts as a detersive agent. Cetylpyridinium chloride also acts as a potentiator of the antimicrobial properties of sodium benzoate. Cetylpyridinium chloride has been shown to be a powerful, rapidly acting germicide against test bacteria in vitro (Helmsworth and Hosworth, 1045), particularly against staphylococci. Cetylpyridinium chloride killed *Pseudomonas aeroginosa* in 10 minutes at 37° C. in a minimum dilution of 1:5800, which was a more concentrated solution than was required to kill a variety of other gram-negative bacteria and cocci (Quisno and Foster, 1946). Work with cetylpyridinium chloride has illustrated several common characteristics of quaternary ammonium compounds, such as their greater activity against gram-positive bacteria than against gram-negative bacteria (Quisno and Foster, 1946).

The following table shows the germicidal activity of cetylpyridinium chloride aqueous solution at 37° C.

GERMICIDAL ACTIVITY OF CETYLPYRIDINIUM
CHLORIDE AQUEOUS SOLUTION

| Organism | Number of Strains Tested | Average Critical Killing Dilution in Terms of Active Ingredients at 37° C. (No Serum) |
| --- | --- | --- |
| Staphyloccus aureus | 5 | 1:83,000 |
| Staphyloccus albus | 2 | 1:73,000 |
| Streptococcus viridans | 1 | 1:42,500 |
| Streptococcus hemolyticus | 2 | 1:127,500 |
| Neisseria catarrhalis | 2 | 1:84,000 |
| Diplococcus pneumoniae | 1 | 1:95,000 |
| Pseudomonas aeruginosa | 2 | 1:5,800 |
| Klebsiella pneumoniae | 2 | 1:49,000 |
| Coronebacterium diptheriae | 1 | 1:64,000 |
| Mycobacterium phlei | 1 | 1:1,500 |
| Eberthella typhosa | 5 | 1:48,000 |
| Escherichia coli | 2 | 1:66,000 |
| Proteus vulgaris | 2 | 1:34,000 |
| Shigella dysenteriae | 1 | 1:60,000 |
| Shigella paradynsenteriae (Flexner) | 2 | 1:52,000 |
| Shigella paradysenteriae | 1 | 1:49,000 |
| Shigella sonne | 2 | 1:68,000 |

The mouthwash is prepared by mixing the active ingredients together to form a homogeneous solution. The manner of making the invention is illustrated in the following example. A mouthwash was formulated from the following components in the indicated weight percentages:

| COMPONENT | WEIGHT % |
| --- | --- |
| Phase A-1 | |
| Water | 79.0538 |
| Glycerine, FCC | 19.00 |
| Phase A-2 | |
| Sodium Benzoate, FCC | 0.30 |
| Citric Acid, FCC | 0.10 |
| Cetylpyridinium chloride, FCC | 0.045 |
| Phase B | |
| Flavor (cinnamon and mint) | 0.40 |
| maltol, FCC | 0.10 |
| xylitol | 1.00 |
| FDC red #40, 1% solution | 0.12 |

The main mixing vessel was a clean, sanitized, stainless steel (304 or 316 - grade) steam-jacketed manufacturing tank, equipped with a lightning type mixer. The tank was charged with water, which was mixed with moderated agitation in order to prevent foaming, and heated to a temperature no higher than 60° C. The phase A-2 ingredients then were added very slowly, in sequence, and cooled gradually until all powdered materials had dissolved, After the temperature had dropped to below 50° C., the glycerine (a Phase A-1 ingredient) was added to the batch. A second, clean, sanitized, stainless steel vessel was charged with the remainder of the water; the temperature of the water was no higher than 40° C. After further cooling, the batch was clear. The resultant product was uniform in appearance and did not separate, even after prolonged standing at room temperature.

Further modifications to the invention may be made without departing from the spirit and scope of the invention; accordingly, what is sought to be protected is set forth in the appended claims.

We claim:

1. A mouthwash which is effective to assist in removal of dental plaque consisting of: water, glycerin, sodium benzoate, cetylpyridinium chloride, citric acid, maltol, xylitol, a flavoring agent, and a coloring agent, said composition being free of alcohol, sugar and artificial sweetener said composition being free of any alcohol, sugar, or artificial sweeteners.

2. The mouthwash of claim 1 wherein the percentage by weight of the composition is: water about 79.0538%, glycerin about 19.00%, sodium benzoate about 0.30%, cetylpyridinium chloride about 0.045%, citric acid about 0.10%, maltol about 0.10%, xylitol about 1.00% flavoring agent about 0.40%, and coloring agent about 0.0012%.

3. An antimicrobial, antiplaque mouthwash consisting of: a first antimicrobial agent with antiseptic properties which also acts as a preservative and an antiplaque agent, a second antimicrobial agent which also possesses antiseptic properties and acts as a detersive agent, a buffering agent, a humectant, a nutrient, a flavoring and fragrance agent, a coloring agent and a carrier, said composition being free of alcohol, sugar and artificial sweetener said composition being free of any alcohol, sugar, or artificial sweeteners.

4. The mouthwash of claim 3 wherein said first antimicrobial agent is sodium benzoate.

5. The mouthwash of claim 4 wherein said second antimicrobial agent is cetylpyridinium chloride.

6. The mouthwash of claim 5 wherein said buffering agent is citric acid.

7. The mouthwash of claim 6 wherein said humectant is glycerin.

8. The mouthwash of claim 7 wherein said carrier is water.

9. The mouthwash of claim 8 wherein said flavoring and fragrance agent is maltol.

10. The mouthwash of claim 9 wherein said nutrient is xylitol.

11. The mouthwash of claim 10 wherein said flavor is mint and cinnamon.

12. The mouthwash of claim 3 having a pH of 6.6±0.4.

13. A dental rinse composition for loosening and removing plaque from dental surfaces consisting of an aqueous carrier for the ingredients of said composition, said ingredients including water about 79% by weight, glycerin about 19.00% by weight, sodium benzoate about 0.30% by weight, cetylpyridinium chloride about 0.045% by weight, citric acid about 0.10% by weight, maltol about 0.10% by weight, xylitol about 1.00% by weight, flavoring agent about 0.40% by weight, and coloring agent about 0.0012% by weight, said composition being free of alcohol, sugar and artificial sweetener said composition being free of any alcohol, sugar or artificial sweeteners.

14. The dental rinse of claim 13 wherein said flavoring agent consist of mint 85% and cinnamon 15%.

15. An antimicrobial, antiplaque mouthwash consisting essentially of an aqueous carrier, less then 20% glycerine, minor effective amounts of colorant and flavorant, less than 1% sodium benzoate and cetylpyridinium chloride, about 1% xylitol, and an effective amount of maltol, said composition being free of alcohol, sugar and artificial sweetener said composition being free of any alcohol, sugar, or artificial sweeteners.

* * * * *